United States Patent [19]

Langdon

[11] 4,447,411

[45] May 8, 1984

[54] CONTROLLING UNDESIRED GROWTH OF MOLLUSKS

[75] Inventor: Christopher J. Langdon, Lewes, Del.

[73] Assignee: University of Delaware, Newark, Del.

[21] Appl. No.: 362,211

[22] Filed: Mar. 26, 1982

[51] Int. Cl.³ ............................................. A61K 9/50
[52] U.S. Cl. ....................................... 424/14; 424/16; 424/19; 424/31; 424/143; 424/149; 424/1.1; 428/402.2; 428/402.24; 71/DIG. 1
[58] Field of Search .................. 428/402.2, 402.24; 424/34, 38, 19, 14

[56] References Cited

U.S. PATENT DOCUMENTS

| | | | |
|---|---|---|---|
| 3,336,155 | 8/1967 | Rowe | 428/402.24 X |
| 3,493,652 | 2/1970 | Hartman | 424/38 X |
| 3,985,840 | 10/1976 | Hofacker | 428/402.2 X |
| 4,253,877 | 3/1981 | Miale et al. | 428/402.24 X |
| 4,286,020 | 8/1981 | Himel et al. | 428/402.24 X |

*Primary Examiner*—Richard D. Lovering

[57] ABSTRACT

Microencapsulated biocides and adductor muscle relaxants for control of undesirable mollusks by feeding same to said mollusks.

3 Claims, No Drawings

CONTROLLING UNDESIRED GROWTH OF MOLLUSKS

DESCRIPTION OF INVENTION

This invention relates to a method for controlling the undesired growth of mollusks.

The Asiatic clam is fouling the intake pipes of power stations and is a potential threat to waterways due to its ability to rapidly colonize and thrive in a wide range of different habitats. Accordingly, it is an objective of this invention to provide means for killing or controlling such mollusks as Corbicula.

Corbicula is often found in dense populations, forming beds 3 to 4 feet in depth, along the sides of the intake vaults of power stations. Unless the animals are removed manually at least once a year, live clams and empty shells >19 mm in size tend to become dislodged from the vault area and are carried through the intake system and then block the condenser tubes. Manually clearing the clams from the intake vault involves shutting down the power unit, dewatering the system and employing workmen to remove the clams physically. This procedure is costly in both generating time and manpower. It is estimated that such clam control for a single power station costs $25,000 to $50,000 per year.

The control of Corbicula using biocides freely dissolved in intake waters has not been wholly successful, mainly because Corbicula is able to sense an irritant biocide and then close up its shell, so protecting itself from the adverse conditions. Corbicula has therefore been found to be surprisingly resistant to heavy metal exposures and chlorination (Gross, L. B., J. M. Jackson, H. B. Flora, B. G. Isom, C. Gooch, S. A. Murray, C. G. Burton and W. S. Bain. 1979. Control studies on Corbicula for steamelectric generating plants. J. C. Britton (Ed.), Texas Christian University Research Foundation, Forth Worth, Texas; Cherry, D. S., J. H. Rodgers, R. L. Graney and J. Cairns. 1980. Dynamics and control of the Asiatic clam in the New River, Va. Virginia Water Resources Research Center, Virginia Polytechnic Institute and State University, Blacksburg, Va. 24060). For example, Cherry et al. 1980, found that Corbicula could tolerate a 96 hour exposure to chlorine levels as high as 20 mg/l (total residual chlorine, TRC) without mortality occurring. Only exposures of ten days yielded significant mortalities ($LC_{50}$ occurred at a TRC of 0.69 mg/l).

This invention proposes to control the undesirable clams by using either microencapsulated biocides or microencapsulated adductor muscle relaxants that either kill the animal or render it susceptible to low level chlorination treatment as an alternative to the intermittent and costly method of control of the Asiatic clam presently employed.

The application and advantages of microencapsulated control agents are:

(1) the agent remains encapsulated in an innocuous material whilst the animal is feeding and ingesting the capsules and it will therefore be unable to sense its harmfulness and will not respond by closing up its valves. Once the capsules are ingested, breakdown of the capsule wall will occur which will then release the capsules' contents into the animal's gut. Absorption of the capsules' contents will result in the clam's death or the relaxation of the adductor muscle. Relaxation of the adductor muscle will make the clam more susceptible to chlorine or other dissolved chemicals as it will be unable to respond by closing its valves. The agent released in the gut of the clam will continue to act, even if the clam closes up.

(2) The encapsulated agent is concentrated from the surrounding water by the filtration process of the clam. A much smaller total amount of the agent needs to be added to the water in order to affect the clam than if the agent was simply added to the water in a non-encapsulated form. Furthermore, the agent within the capsule is highly concentrated. Thus, administration of a very wide variety of potential molluscicides is possible and wastage and environmental impact is minimized.

(3) The pH and other chemical conditions of the internal aqueous phase of certain types of capsules can be controlled. By this means regulating the rate of decomposition of the encapsulated agent can be effected. The rate of hydrolysis of many organophosphorus pesticides, for example, is dependent on pH. By adjusting the pH of the internal phase containing the organophosphorous compound, the rate of its breakdown can be adjusted as required assuring that the environmental impact of any capsules uneaten by Corbicula is minimized.

(4) It is possible to further reduce capsule wastage and hence environmental impact by determining the optimum dose level, as well as the best rate and conditions of application for any particular site. These parameters can be determined before the addition of the encapsulated control agent, by pilot experiments which measure the removal of stained, nontoxic capsules by filter feeding organisms in the intake pipe of the power station. Knowing this, it would then be possible to either adjust the capsule dosage or the conditions of application to minimize wastage.

(5) Capsule ingestion and effectiveness of the dose may be stimulated by simultaneous food ingestion.

(6) Short pulse (minutes to hours) administration of capsules may prove highly effective.

This invention uses a capsule with an oil or wax wall for encapsulation of water-soluble agents and a coacervate walled capsule for the encapsulation of water-insoluble agents. The oil or wax walled capsule uses a substance for the wall of the capsule that is immiscible with water and can be broken down in the gut of the target organism. Examples of suitable wall materials are edible-oils, e.g., menhaden oil, waxes, silicone-oils and paraffin-oils. Capsules in the size range 2 to 15 μm in diameter have been prepared which have been shown to trap 6 to 10% by volume of an aqueous phase. Phenol red, $^{14}C$ labelled glycine and $^{14}C$ labelled lysine are retained in the capsule for at least one month, suggesting that leakage is minimal.

The oil/wax wall capsules are simply prepared by a process of double emulsification. For example, one volume of an aqueous solution of the biocide or adductor muscle relaxant may be dissolved in an aqueous solution of 10% w/v gum acacia and 1 M $CaCl_2$, and emulsified in 4 parts of an oil such as menhaden oil containing 10% w/v ethyl cellulose. The primary emulsion may then be cooled to 5° C. to harden the menhaden oil. One volume of the emulsion may then be emulsified in 4 volumes of a 10% w/v acacia/1 M $CaCl_2$ aqueous solution. The secondary emulsion being made up of droplets of the menhaden oil with droplets of the aqueous biocide or adductor muscle relaxant solution trapped inside. The capsule suspension may be then washed free of $CaCl_2$ and non-encapsulated biocide or adductor muscle relaxant by successive dialysations at 5° C.

The wax wall for the capsules may be prepared in a similar way to the oil wall, except that the temperature at which the capsules are prepared is raised so that the wax melts and forms a liquid during the emulsification steps. After the secondary emulsification, the capsule suspension can be cooled to solidify the wax walls. It should be noted that ethyl cellulose is not necessary in the wax wall formation.

Coacervate walled capsules such as gelatin/acacia walled capsules can be used for encapsulation of water immiscible biocides and adductor muscle relaxants. For example, gelatin/acacia walled capsules may be prepared by a method based on that described by Green and Schleicher in their U.S. Pat. No. 2,800,457 granted July 23, 1957. The water immiscible phase to be encapsulated is first emulsified in acacia and gelatin. The pH of the mixture is then reduced to 4.2 causing the acacia and gelatin to precipitate out in a complex surrounding the emulsion droplets. The pH is then increased to 9.8 and the capsule suspension diluted with 4 parts of water. The capsules can be readily concentrated by centrifugation.

Other types of coacervates apart from gelatin-acacia can be used for wall formation (e.g., methyl cellulose and egg albumen).

The agents that may be encapsulated for the control of Corbicula fall into two categories. Firstly, there are compounds that have general biocidal activity and are chosen for their potential usefulness in killing Corbicula. For these to be effective, a lethal amount of encapsulated biocide must be ingested before filtration and feeding activity cease. Alternatively, the ingested dose of biocide may be effective in that it causes Corbicula to gape uncontrollably which would render it susceptible to low level chlorination treatment. Secondly, there are the adductor muscle relaxants that are expected to affect the adductor muscle of the clam and cause it to gape uncontrollably. The neurophysiology and pharmacology of molluscan smooth muscle, as found in the adductor muscles of bivalves, has been reviewed by Wilbur K. M. and C. M. Younge. 1966. Physiology of the mollusca. Academic Press. The adductor muscle is stimulated to contract by the action of acetylcholine. Contractions are of two types: short, phasic contractions followed by rapid relaxation or prolonged tonic contractions followed by a more gradual relaxation. Relaxation of molluscan smooth muscle after tonic contraction can be brought about by perfusing a muscle preparation with very low levels ($10^{-9}$ M) of 5-hydroxytryptamine (5HT). 5HT relaxes the muscle by abolishing the tonic response; its presence does not, however, eliminate short-term phasic responses. 5HT is not, therefore, considered to be an inhibitor of acetylcholine, but relaxes the 'catch' mechanism that is responsible for the prolonged tonic contraction of the muscle.

Prevention of prolonged shell closure by tonic contraction could be attained by either blocking the action of acetylcholine or by relaxing the adductor muscle by 5HT or a similarly acting agent. The acetylcholine blocking agent must be present before the muscle is stimulated to tonically contract, since once it is in this state, further excitation by the action of acetylcholine appears to be unnecessary for the maintenance of the contraction.

Biocides that may be used in this invention are copper sulphate, trichlorfon, chlordimeform, and frescon. Muscle relaxants that may be used in this invention are methantheline bromide, reserpine, and 5-hydroxytryptamine. Of the above compounds, frescon and reserpine would be used in coacervate walled capsules and the remainder used in oil or wax wall capsules. These biocides and muscle relaxants may be more fully described as follows:

Copper sulphate (molluscicide, herbicide and fungicide)

$CuSO_4$

Soluble in water (31.6 g/100 mls). Effective against Corbicula when added in solution $LC_{50}$ 0.04 mgs/l. A commonly used molluscicide but also toxic to fish and plants. Half life of the toxic $Cu^{2+}$ ion in 'natural' waters has been reported to be as little as 5 hours, since complex formation with silt and organic particles renders it non-toxic. The potentially low levels of application of the encapsulated $CuSO_4$ and reduced wastage of capsules will further reduce environmental impact.

Trichlorfon (an organophosphorus pesticide)

O,O-Dimethyl (1-hydroxy-2,2,2-trichloroethyl) phosphonate $(CH_3O)_2PO.CH(OH)CCl_3$ Soluble in water (15.4 g/100 mls) at 0° C. Insoluble in petroleum oils, soluble in ether, chloroform and benzene. Short half life. In 70% ethanol —pH 6.0 buffer solution (1:4) trichlorfon has a half life of 3.2 hours. Its rate of decomposition (hydrolysis) is dependent on pH, however, and increases as the pH becomes more alkaline or acidic. When encapsulated inside an oil or wax walled capsule, it will therefore be possible to shorten its half life by adjusting pH if necessary.

Chlordimeform (acaricide)

N-(2 methyl-4-chlorophenyl)-N',N'-dimethyl formamidine

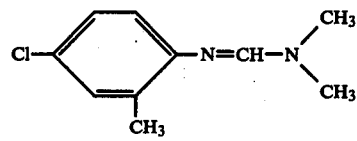

The hydrochloride salt is >50% w/w soluble in water and insoluble (0.1%) in benzene.

Frescon (molluscicide)

N-trityl-morpholine

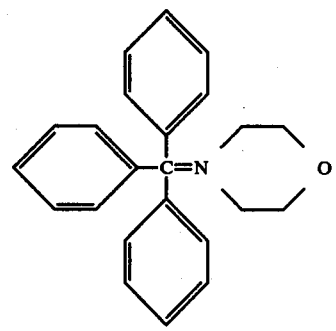

Frescon is sparingly soluble in water (0.02 ppm at 20° C.), but soluble in most organic solvents at 20° C., such as chloroform (4–5%), carbon tetrachloride (30%) and tetrachlorethylene (20.5%). Encapsulation of Frescon dissolved in lipid droplets using coacervate walled capsules should be the best method of application.

Methantheline bromide (Banthine bromide)

Diethyl (2-hydroxyethyl) methyl ammonium bromide xanthene-9-carboxylate.

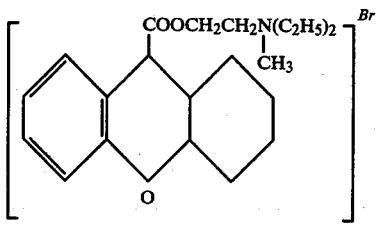

A water soluble anticholinergic agent. This agent blocks the action of actelycholine in molluscan smooth muscle.

5-hydroxytryptamine (5HT)

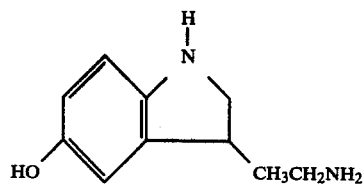

The hydrochloride of 5HT is soluble in water and stable at pH's 2–6.4.

Reserpine 3,4,5-Trimethoxybenzoyl methyl reserpate

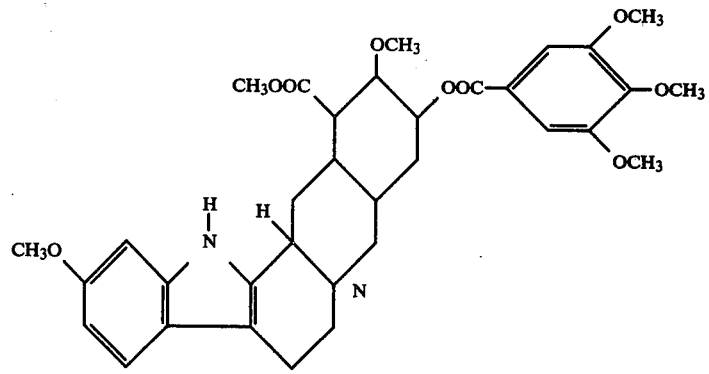

Reserpine is used in medicine as a tranquilizing agent. It has the effect of preventing the binding and storage of 5HT at the sites of synthesis.

5HT is, therefore, constantly released. Reserpine has been found effective in relaxing molluscan smooth muscle. Reserpine is slightly soluble in aqueous solutions of acetic and citric acid and soluble in chloroform, benzene and ethyl acetate. This agent may therefore be encapsulated either dissolved in the aqueous phase of the oil/wax membrane capsules or dissolved in the lipid phase of coacervate wall capsules.

I claim:

1. The method of controlling undesirable mollusks which comprises the steps of releasing in their feed waters a microencapsulated adductor muscle relaxant, and subjecting the mollusks to a biocide after the adductor muscle relaxant takes effect.

2. The method of claim 1 wherein the muscle relaxant is selected from the group consisting of methantheline bromide, reserpine, and 5-hydroxytryptamine.

3. The method of claim 1 wherein the biocide is selected from the group consisting of chlorine, copper sulphate, trichlorfon, chlordimeform and frescon.

* * * * *